US006639665B2

(12) United States Patent
Poole (10) Patent No.: US 6,639,665 B2
(45) Date of Patent: Oct. 28, 2003

(54) MULTISPECTRAL IMAGING SYSTEM FOR CONTAMINANT DETECTION (75) Inventor: Gavin H. Poole, Slidell, LA (US)

(73) Assignee: Institute for Technology Development, Jackson, MS (US)

( * ) Notice: Subject to any disclaimer, the term of this patent is extended or adjusted under 35 U.S.C. 154(b) by 110 days.

(21) Appl. No.: 09/779,706

(22) Filed: Feb. 9, 2001

(65) Prior Publication Data
US 2002/0135760 A1 Sep. 26, 2002

(51) Int. Cl.$^7$ .................................................. G01J 3/00
(52) U.S. Cl. .................. 356/300; 356/317; 250/223 R; 209/576
(58) Field of Search ...................... 356/300; 250/223 R; 209/539, 540, 541, 542, 576, 577, 580, 581, 582, 587, 701; 452/177, 178, 179, 184; 198/860.1, 860.2, 860.3, 860.4, 860.5

(56) References Cited

U.S. PATENT DOCUMENTS

| 4,239,969 A | * | 12/1980 | Haas et al. .................... 378/57 |
| 4,839,522 A | * | 6/1989 | Bourgeois et al. ...... 250/455.11 |
| 5,428,657 A | * | 6/1995 | Papanicolopoulos et al. . 378/86 |
| 5,488,479 A | | 1/1996 | Williams et al. ............ 356/402 |
| 5,621,215 A | | 4/1997 | Waldroup et al. ......... 250/461.2 |
| 5,821,546 A | | 10/1998 | Xiao et al. ................... 250/458 |
| 5,895,921 A | | 4/1999 | Waldroup et al. ......... 250/461.2 |
| 5,914,247 A | | 6/1999 | Casey et al. .................. 435/34 |
| 6,114,699 A | | 9/2000 | Barton et al. .......... 250/339.09 |

OTHER PUBLICATIONS

B. Park, Y. R. Chen, M. Ngyuen, "Multi–spectral image analysis using neural network algorithm for inspection of poultry carcasses", J. Agric. Engng Res., vol. 69, pp. 351–363, 1998.*

"Sorting Cut Roses with Machine Vision" V. Steinmetz et al, 1994 ASAE, vol. 37(4); 1347–1354.
"Multispectral Image Textural Analysis for Poultry Carcasses Inspection" Bosoon Park et al, ASAE, Paper No. 946027 (1994).
"An Automated Corn Kernel Inspection System Using Machine Vision" by Bincheng Ni et al, ASAE/CSAE Meeting Presentation, Paper No. 933032, 1993.
"Hyperspectral Imaging For Detecting Bruises in Apples" Renfu Lu et al, Paper 993120 ASAE Meeting, 1999.
"Multi–spectral Image Analysis using Neural Network Algorithm for Inspection of Poultry Carcasses", B. Park et al, 1998 J. Agric. Engng Res. 69, 351–363.
"Application of hyperspectral imaging spectrometer systems to industrial inspection" Charles T. Willoughby et al, pps. 264–270/SPIE Vo. 2599.
"Real–Time Multispectral Image Processing For Poultry Inspection" B. Park et al, ASAE Meeting Presentation, Paper No. 983070, 1998.
"Characterizing Multispectral Images of Tumorous, Bruised, Skin–Torn, and Wholesome Poultry Carcasses", B. Park et al, ASAE, vol. 39(5); 1933–1941 (Jun. 1996).

(List continued on next page.)

Primary Examiner—Thong Nguyen
Assistant Examiner—Arnel C. Lavarias
(74) Attorney, Agent, or Firm—Crowell & Moring LLP (57) ABSTRACT An automated inspection system for detecting digestive contaminants on food items as they are being processed for consumption includes a conveyor for transporting the food items, a light sealed enclosure which surrounds a portion of the conveyor, with a light source and a multispectral or hyperspectral digital imaging camera disposed within the enclosure. Operation of the conveyor, light source and camera are controlled by a central computer unit. Light reflected by the food items within the enclosure is detected in predetermined wavelength bands, and detected intensity values are analyzed to detect the presence of digestive contamination.

23 Claims, 6 Drawing Sheets

OTHER PUBLICATIONS

"Multispectral Image Co-occurrence Matrix Analysis for Poultry Carcasses Inspection", B. Park et al, ASAE, vol. 39(4); 1485–1491 (Paper No. 94–6027).

"Texture Analysis of Aerial Photographs" Ronald Lumia et al, Pattern Recognition vol. 16, No. 1, pp. 39–46, 1983.

"Commercial Near–Infrared Reflectance Analyzers", P.C. Williams et al (1987) Commercial Analyzer, pps. 107–141.

"Leaf Nitrogen Analysis of Poinsettia (*Euphorbia pulcherrima Will D.*) Using Spectral Properties in Natural and Controlled Lighting" G.E. Meyer et al, ASAE vol. 8(5); Sep. 1992 pp 715–722.

"A Color Vision System for Peach Grading" Byron K. Miller et al, ASAE, 1989, pps 1484–1490.

"The Nature of Remote Sensing" Chapter 1, Schowengerdt, R.A. 1997, pp. 1–33.

"Machine Vision for Color Inspection of Potatoes and Apples" Y. Tao et al, ASAE, vol. 38(5); 1555–1561.

"Hyperspectral imaging for safety inspection of food and agricultural products" Renfu Lu et al, SPIE vol. 3544, Nov. 5, 1998, pps. 121–133.

"Intensified Multispectral Imaging System For Poultry Carcass Inspection" B. Park et al, ASAE Nov./Dec. 1994, vol. 37, No. 6, pp 1983–1988.

"Spectral imaging in biomedicine: A selective overview", Richard M. Levenson et al, SPIE vol. 3438, Jul. 1998, pps. 300–312.

* cited by examiner

MULTISPECTRAL IMAGING SYSTEM FOR CONTAMINANT DETECTION

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Specific Cooperative Agreement No. 58-6612-9-023 awarded by the National Aeronautics and Space Administration ("NASA").

BACKGROUND AND SUMMARY OF THE INVENTION

The present invention relates to an optical system for detecting the presence of contaminants in food items during processing. More particularly, the invention is directed to the detection of ingesta and fecal contamination which may be present on poultry carcasses being processed on a conveyor system in a poultry processing plant.

In 1997, there were 76 million reported cases of food borne illnesses in the United States, which resulted in approximately 5,000 deaths. This means that at least one out of every four United States residents suffered from some form of illness that could be attributed to the consumption of food products. It is thus apparent that the incidence of food borne illnesses is significant even in a highly developed economy, and that the prevention of such diseases is a matter of great importance and urgency. The foods most likely to be responsible for the transmission of diseases caused by common bacterial pathogens are animal products such as red meats, poultry, eggs, seafood and dairy products.

Contamination of meat and poultry products can occur, for example, as a result of exposure to ingesta and fecal material in a food processing plant during or after slaughtering. Accordingly, in order to minimize the likelihood of such contamination, it has been necessary to examine each food item individually to detect the presence of contaminants. Historically, such inspection has been performed visually by U.S.D.A. inspectors, who examine each individual food item as it passes through the processing system.

In a modern poultry processing plant, chicken carcasses are placed on a processing line conveyor system for dressing and inspection. Typically, such conveyors operate at speeds on the order of 100 carcasses per minute, with a six inch separation between shackles. Even with two inspectors continuously performing such inspection, only about two seconds are allotted for the inspection of each carcass.

During these two second inspections, the inspector is required to check for evidence of eight different diseases as well as for certain quality characteristics, to verify that the chicken was live when placed on the production line, and to check for evidence of ingesta or fecal contamination. Moreover, during a typical business day operating in two eight hour shifts, a productive poultry processing plant may produce as many as 250,000 processed chickens.

It is apparent from this brief description that the historical visual inspection of poultry carcasses by human inspectors is problematic, and that it is poorly suited to the effective detection and elimination of contaminants in modern poultry processing plants. In particular, it requires the inspectors to make a subjective determination repeatedly at intervals of less than two seconds throughout an eight hour shift. Such a system is prone to errors, which can lead to the entry of contaminated poultry products into the commercial distribution system.

In view of these deficiencies in the historical visual inspection technique, efforts have been made to develop automated or semiautomated systems for detecting the presence of contaminants in meat, poultry and other food products during processing. Most such systems utilize a technique in which the food item is irradiated with light having a frequency (for example, in the UV range) such that it causes the emission of fluorescent radiation upon striking fecal matter or ingesta. Fluorescent light emanating from the target food item is then measured and compared with a threshold value. If the light thus gathered exceeds the threshold, a signal indicative of the presence of fecal contamination or ingesta is generated. Such a system is disclosed, for example in U.S. Pat. Nos. 5,621,215 and 5,895,921 to Waldroup et al and U.S. Pat. No. 5,821,546 to Xiao et al.

U.S. Pat. No. 5,914,247 to Casey et al discloses a fecal and ingesta contamination detection system which is based on the premise that the emission of fluorescent light having a wavelength between about 660 and 680 nm is indicative of the presence of ingesta or fecal material. Thus, carcasses being processed are illuminated with UV or visible light (suitable wavelengths being between 300 and 600 nm) and the illuminated surface is then examined for the emission of fluorescent light in the 660 to 680 nm range. In a preferred embodiment, the intensity of such fluorescence in the 660–680 nm range is compared with that in the 610–620 nm range as a baseline in order to distinguish fluorescent light emissions of the carcasses themselves.

One object of the present invention is to provide an improved process and apparatus for detection of ingesta and fecal contamination on a food item, which achieves enhanced accuracy and dependability in positively identifying such contaminants. Ingesta and fecal material are sometimes referred to generically herein as "digestive contamination," which term is used to refer to all content of the digestive tract or alimentary canal.

Another object of the invention is to provide a process and apparatus which can reliably detect such contaminants at a speed which is compatible with the rate at which chicken carcasses are processed on a modern production line.

Still another object of the invention is to provide a method for processing light reflected from a food item, which method produces a signal that reliably indicates the presence of ingesta and fecal contamination, and an apparatus which implements such method.

Yet another object of the invention is to provide a food stuff inspection system having an enclosure which excludes ambient light from a portion of a conveyor system in a food processing production line, in which light having a preselected spectral content can be used to illuminate food items which are being inspected.

Finally, another object of the invention is to provide an automated food inspection system which can quickly and accurately identify contaminated food items in a food processing line.

These and other objects and advantages are achieved by the method and apparatus according to the present invention in which a portion of a poultry processing conveyor line is passed through a light excluding enclosure which excludes ambient light. Inside the enclosure, each carcass is illuminated by a light source which emits light having a preselected spectral content as the carcass passes before a multispectral digital imaging camera. The camera acquires a multispectral digital image of each chicken carcass, including digital numbers indicative of reflectance values for each pixel in an optical sensor array, in each of several preselected frequency bands.

A digital camera suitable for this purpose may be, for example, a multispectral CCD (charge coupled device) camera, in which light collected by the camera lens is split into a plurality of spectral components or "optical channels", each of which is focused on a separate CCD array. Typically, channel separation is achieved by means of an arrangement of prism elements and optical filters, although other spectral resolving devices may be used. Such cameras are known, and are commercially available, for example, from Duncan Technologies, Inc. of Auburn, Calif.

It is of course possible to achieve similar multispectral digital image data by using multiple digital imaging devices, such as CCD cameras, each having its own filter, for isolation of a preselected wavelength band. In this event, however, additional processing capacity is required in order to adjust for slightly different viewing angles, to control the respective cameras and to assure proper registration of the acquired images.

The multispectral digital image signals provided by the camera system are input to a digital computer via a known "frame grabber" which assembles the data into respective image frame files. These data are then processed by the computer according to either of two processes, including differing processing algorithms and method steps, depending on the nature of the production line processing of the chicken carcasses. The end result of such computer analysis is the generation of a "yes/no" or "good/bad" determination for each carcass which passes in front of the CCD camera, so that those carcasses on which ingesta or fecal contamination is detected can be removed automatically from the processing line for additional special washing procedures to eliminate the contaminants.

An important feature of the present invention is the enclosure of a portion of a processing conveyor in a light excluding compartment in order to achieve accurate control of the spectral content of light which impinges on, and is reflected by, the chicken carcasses which are inspected during processing.

Other objects, advantages and novel features of the present invention will become apparent from the following detailed description of the invention when considered in conjunction with the accompanying drawings.

BRIEF DESCRIPTION OF THE DRAWINGS

FIG. 2b is an end view of the components and light excluding enclosure of FIG. 2a.

FIG. 3 is a schematic diagram which shows the components of the multispectral contamination detection system according to the invention;

DETAILED DESCRIPTION OF THE DRAWINGS

Figure 1:
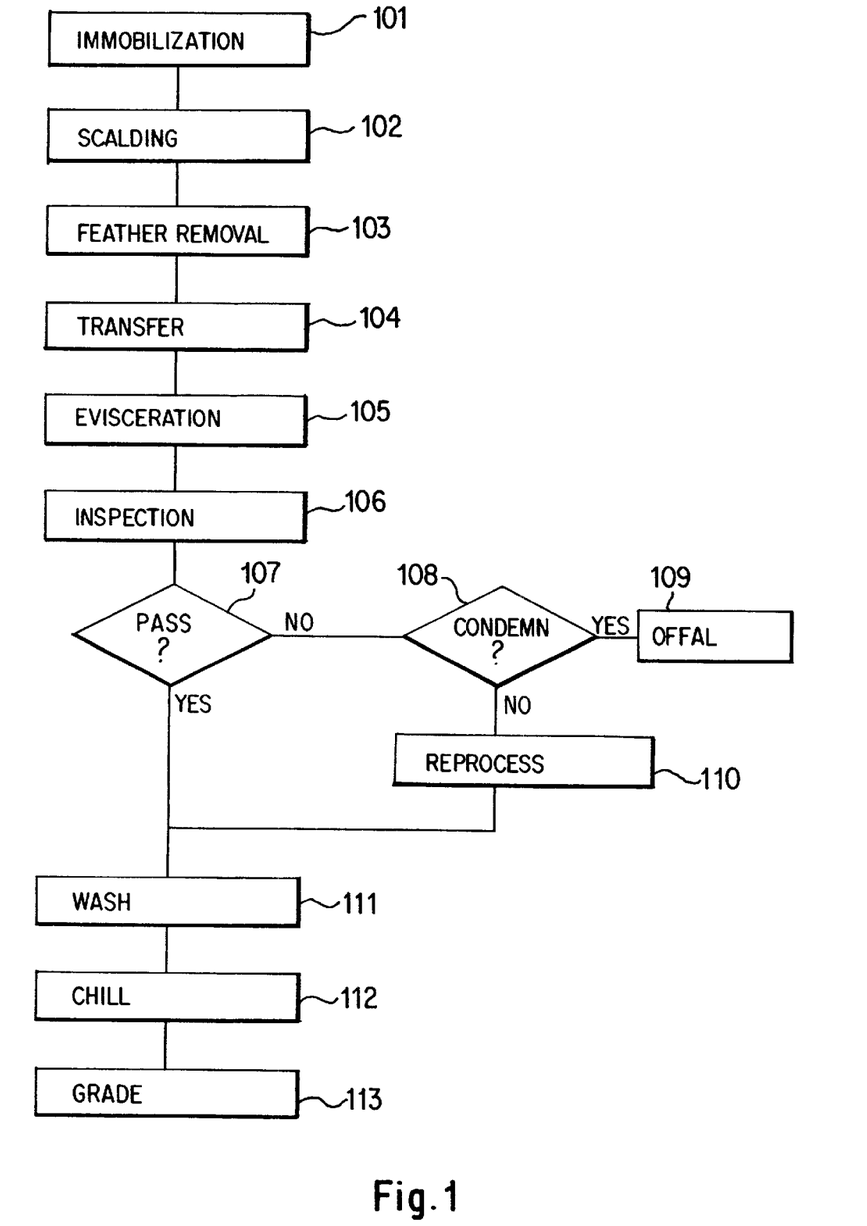
FIG. 1 is a flow chart which illustrates the steps in processing of poultry in a modern processing plant.

FIG. 1 is a schematic diagram which shows the processing of chickens in a poultry processing plant. Upon entry into the plant, chickens are initially immobilized, as indicated in step 101. This includes the process of hanging the chickens on metal shackles, stunning them and slaughtering them. Thereafter, they are scalded as described below, by immersion in hot water (step 102). The feathers are then removed in step 103 by mechanical "pickers" which remove most of the feathers. In addition, the birds are often passed in close proximity to an open flame, to burn off any "filoplumes" (hair-like feathers) which remain.

In step 104, the carcasses are transferred to a separate facility, where they are eviscerated (step 105). In this stage, the carcasses are inspected by USDA inspectors (step 106) and either passed or rejected in step 107. If they are rejected, in step 108 they are either condemned as unfit for human consumption (and sent to offal in step 109) or are reprocessed in step 110 and returned to the processing line. In step 111, the carcasses are passed through a final whole bird washer in which they are rinsed inside and out with high pressure water. Finally, in step 112, the birds are chilled to a temperature below 40° F. by immersion in a water and ice mixture, and thereafter they can be graded by USDA inspectors (step 113).

An important consideration for the purpose of ingesta and fecal contamination detection according to the invention is the manner in which the chicken carcasses are scalded to loosen the feathers. Two alternatives—known as "hard scalding" and "soft scalding"—are commonly used for this purpose. Hard scalding is performed using water at a temperature of 55–60° C. for a period of 30–75 seconds, and is generally more effective in loosening the feathers, but tends also to remove the cuticle layer of skin that give the chicken a deeper yellow color. Soft scalding on the other hand, is performed at a temperature of 50–54.5° C. for a period of 90–120 seconds, and retains the original skin color, but leaves the feathers more firmly attached. Depending on the customer requirements, either process is suitable.

As discussed in more detail hereinafter, the choice as between these two types of scalding dictates which of two alternative processing techniques—including differing processing algorithms—is used to detect contaminants.

Figure 2A:
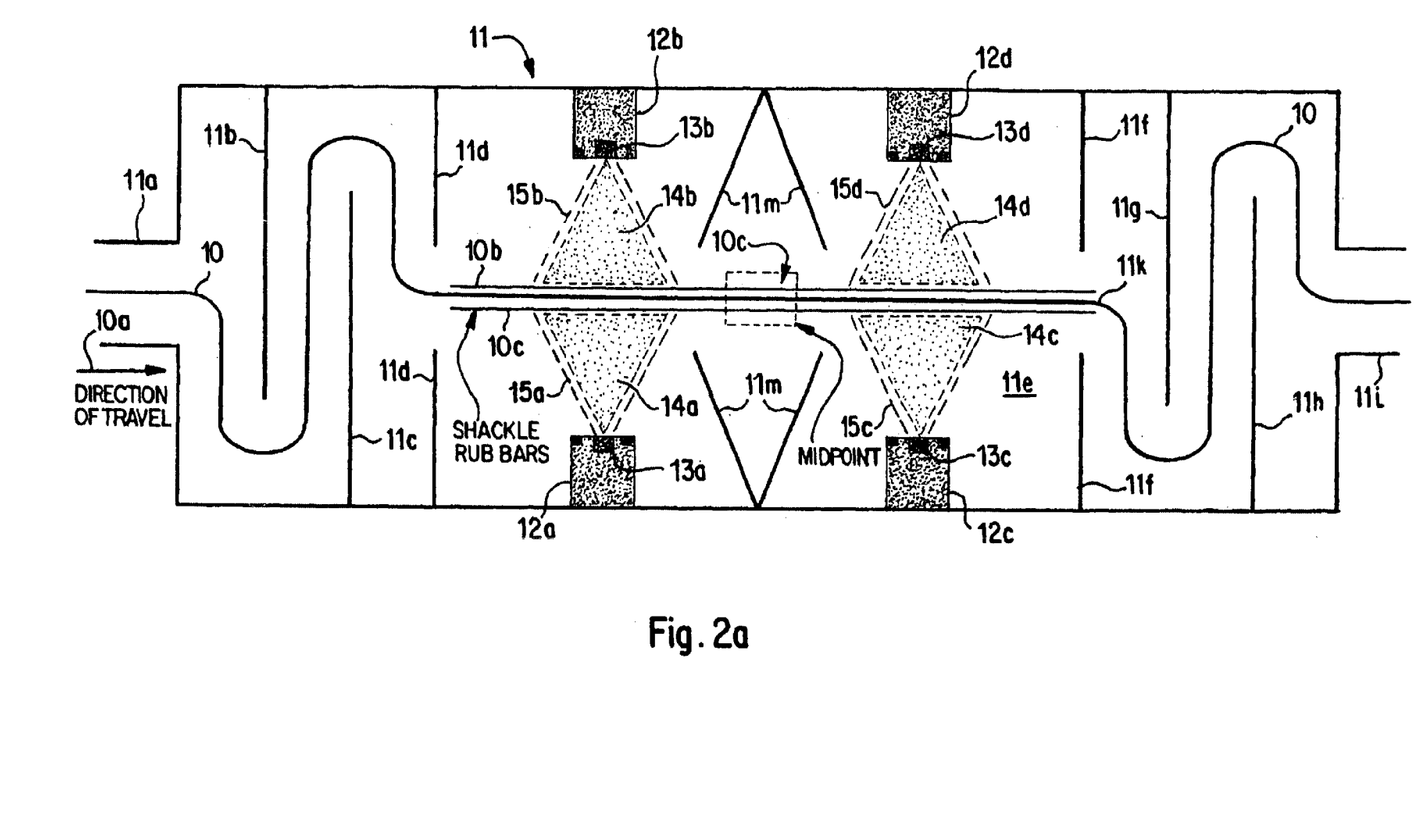
FIG. 2a is a side view schematic depiction of a portion of a poultry processing conveyor line with optical components of the multispectral digital contamination detection system arranged in a light excluding enclosure according to the invention.

FIG. 2a is a schematic illustration which shows the physical layout of the components of the detection system in a light excluding enclosure according to the invention. As described above, chickens are placed on a conveyor system in the form of a shackle line, for progressing through the dressing and inspection process. A portion of the conveyor system 10 is shown in FIG. 2a, and moves in the direction indicated by the arrow 10a. To facilitate detection of contaminants according to the invention, the conveyor line passes through the light excluding enclosure 11.

The conveyor enters the enclosure through an opening 11a, and travels a circuitous route past a series of baffles 11b, 11c, 11d into a central chamber 11e. The purpose of the baffles is to prevent the propagation of ambient light from the exterior of the enclosure into the central chamber 11e. A comparable set of baffles 11f, 11g, 11h is also provided at an exit opening 11i at the opposite end of the enclosure 11, for the same purpose. In order to assure effective blocking of ambient light, the interior surfaces of the enclosure 11, including baffles 11a–11d, 11f–11h, are covered with a light absorbent material with an extremely low reflectivity, such as flat black paint.

Figures 2B, 3:
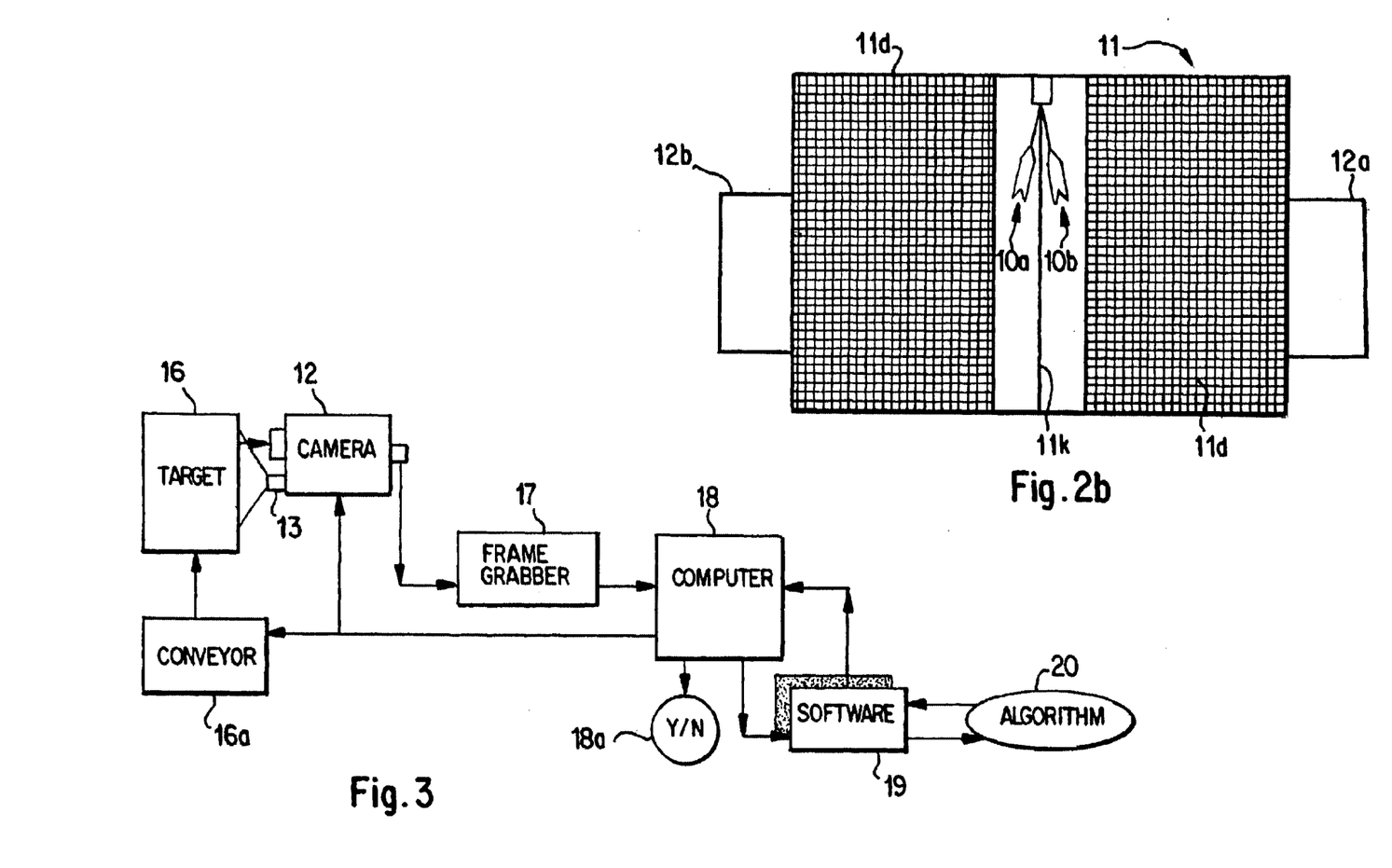

At approximately the point at which the conveyor line 10 passes into the central chamber 11e, the shackles from which the carcasses are suspended are swung alternately to the left and to the right as shown in FIG. 2b, so as to form two parallel lines 10b and 10c, which pass in front of four multispectral digital imaging cameras 12a–12d. The two lines 10a and 10b are separated by an additional baffle 11k, which extends in a vertical plane parallel to the conveyor. At a midpoint 10c along the conveyor line inside the enclosure 11, between the cameras 12a, 12b and cameras 12c, 12d, in a known manner the shackles are rotated 180° about a vertical axis, so that each carcass is rotated correspondingly, exposing the opposite side which previously faced the baffle 11k. In this way, the carcasses carried along line 10a are imaged on a first side by camera 12a and thereafter on the second side by camera 12c, while those on line 10b are imaged on a first side by camera 12b, and on the other side by camera 12d. The baffle ilk prevents light from one side of the enclosure from passing to the other. After the imaging is completed the carcasses pass through the baffles 11f–11h and out of an exit opening 11i.

The cameras 12a–12d may be CCD cameras of the type previously described, each having a field of view 15a–15d, as shown in FIG. 2a. Each such camera has associated therewith a light source 13a–13d which illuminates the carcasses with light having a preselected wavelength suitable for detection purpose, as they move through respective illumination areas 14a–14d. A light source that is color corrected to 5600K is advantageous, although it is apparent that other light sources may be used.

Light reflected from each carcass as it passes through an illumination area 14a–14d within the enclosure 11, through one of the respective fields of view 15a–15d is collected by the multispectral digital imaging cameras 12a–12d. In order to prevent any of the cameras from detecting light scattered from a carcass illuminated in the field of view in an adjacent camera, additional baffles 11m are provided.

Each of the cameras 12a–12d generates multispectral image data which is correlated as between cameras and processed in a computer to generate a binary (yes/no) evaluation of each carcass as discussed hereinafter.

FIG. 3 is a schematic block diagram that shows the components of the detection arrangement according to the invention, in which the camera 12 collects light from a target chicken carcass 16 as it passes through light from the illumination source 13 in the camera's field of view within the light excluding enclosure, as shown in FIG. 2a. A stream of resulting digital signals representative of a multispectral image of the target carcass 16 is supplied from the camera 12 to a "frame grabber" 17, which organizes the data into individual frames or image files which depict the target carcass in each preselected wavelength band. The resulting data files are then input to the computer 18, which process them in a manner described hereinafter in order to generate a "yes/no" or "good/bad" signal 18a for each carcass which is imaged in this manner.

A software program 19 which is stored in a memory of the computer 18 contains the necessary algorithm 20 and process steps for analyzing the acquired image data and drawing a good/bad conclusion as described. It also controls the camera 12 and the processing line (conveyor 16a) in a known manner in order to coordinate their operation.

Figure 4:
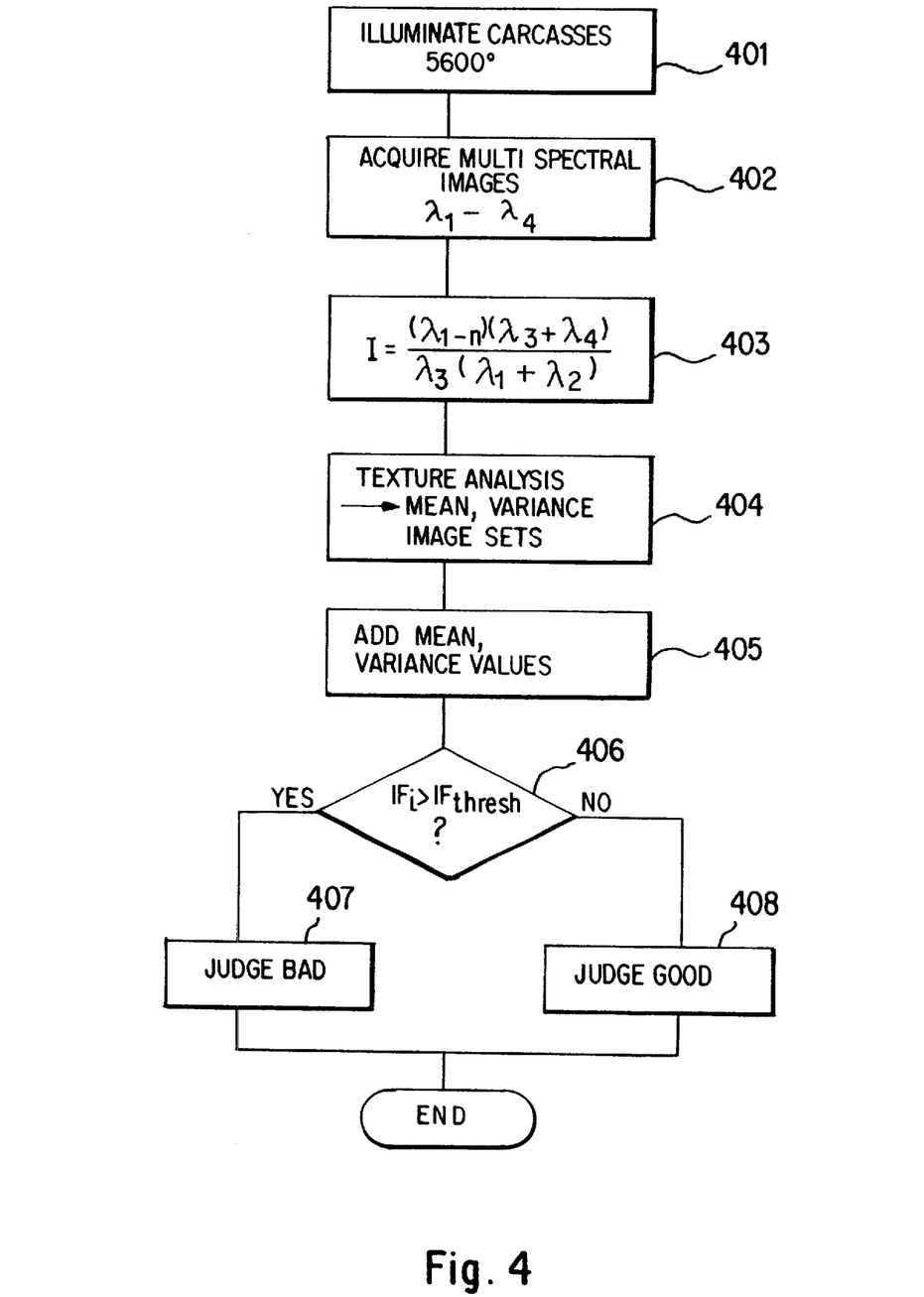
FIG. 4 is a flow chart which illustrates contaminant detection processing according to a first embodiment of the invention.

FIG. 4 is a flow chart which illustrates the steps performed by the method and apparatus according to a first embodiment of the invention, which is advantageously used for detecting ingesta and fecal contamination on carcasses which have been hard scalded prior to removal of feathers. In a first step 401, the carcass is illuminated by a light source which provides a predetermined spectral profile. In this case, it has been determined that a light source corrected to 5600K is particularly advantageous. Since ambient light has been excluded from the interior of the enclosure 11, only light from the light source is reflected from the target carcass.

In step 402, data representing a multispectral image of light reflected from the target carcass are generated by the digital imaging camera 12 in four wavelengths. In particular, it has been determined that the following four wavelength bands are advantageous for this purpose:

$\lambda_1 = 750$–$830$ nm
$\lambda_2 = 450$–$500$ nm
$\lambda_3 = 500$–$535$ nm
$\lambda_4 = 550$–$585$ nm The image data generated in step 402 thus provide four reflectance values, each represented by a digital number (DN), for each pixel included in the acquired image —one such digital number for each of the frequency bands $\lambda_1$–$\lambda_4$. In step 403 these values are combined to generate a value I for each pixel, according to the following algorithm:

$$I = \frac{(\lambda_1 - n)(\lambda_3 + \lambda_4)}{\lambda_3(\lambda_1 + \lambda_2)} \quad \text{(Eq. 1)}$$

wherein n is an integer constant. Subtraction of the constant n in the numerator as indicated in Equation 1, reduces the amount of background noise by altering the DN values of the specified wavelength $\lambda_i$. The result of the above calculation, which is performed in the computer 18 of FIG. 3, is the creation of an image file having a single DN value for each pixel.

Figure 6A:
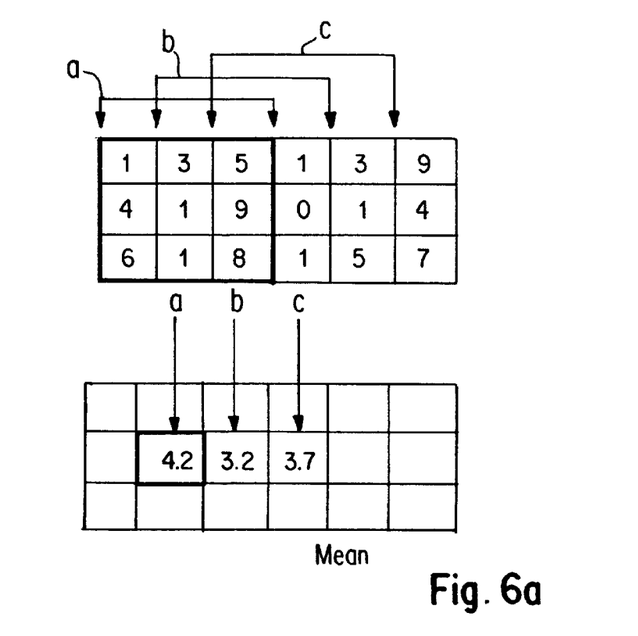
FIGS. 6a and 6b illustrates a digital filtering technique which is common to the first and second embodiments of the invention.
Figure 6B:
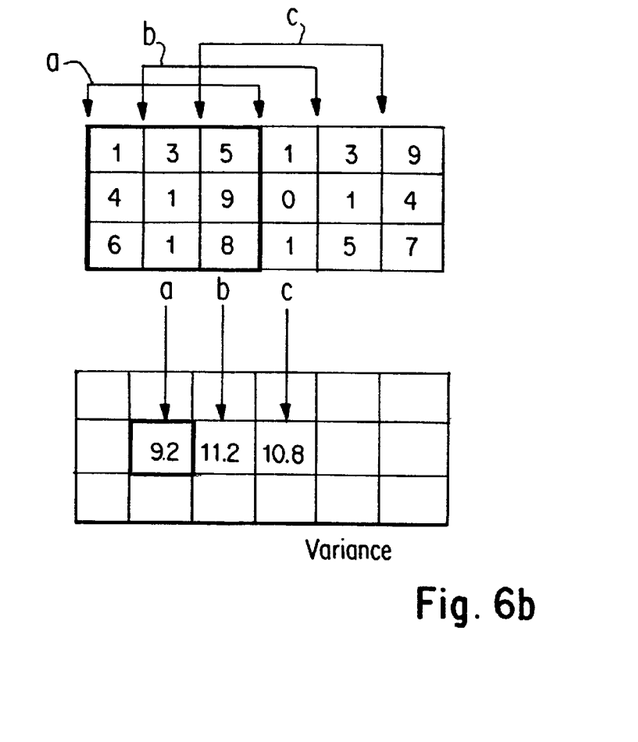

The DN values generated in step 403 are then filtered in step 404 by a process referred to as "texture analysis," which characterizes the image according to areal variations in pixel brightness—that is, DN values—to generate two new output image files indicative of the mean and variance for pixels within a moving window of a 3×3 pixel mask, as illustrated in FIGS. 6a and 6b.

FIG. 6a shows the manner of calculation of mean values in the texture analysis. For each window of nine pixels (a 3×3 pixel set) a mean value of the DN values is determined in a well known manner:

$$\text{mean} = \frac{\sum_{i=1}^{N} x_i}{N} \quad \text{(Eq. 2)}$$

wherein N is the number of data elements $x_i$.

For example, in FIG. 6a, three windows a, b and c are indicated by brackets, with the window a being enclosed by a heavy line. The mean of the DN values in window a, also enclosed by a heavy line, is 4.2. Similarly, the mean value for window b is 3.2 and for window c is 3.7, as also shown in the set of mean values. As the window is moved over the whole of the image file, a complete new image file of mean values is created. It is of course apparent that different sizes and shapes of windows can be used for this purpose.

The technique for calculation of a new image data set of variance values, shown in FIG. 6b, is similar to that used to calculate the mean values, as shown in FIG. 6a and described above. The variance values in FIG. 6b, however are calculated by the following well known formula:

$$\text{Variance} = \frac{\sum_{i=1}^{N}(x_i - \bar{x})^2}{N-1} \quad \text{(Eq. 3)}$$

where N is the number of data elements included in the calculation, and $\bar{x}$ is the mean value of all such data elements.

As is apparent, the performance of the texture analysis in step 404 yields two image data sets, representing the spacially distributed mean and variance values respectively for the data values I calculated in step 403. In step 405, the mean and variance values are added together to form a final output image data set IF.

Finally, in step 406, the image data set IF is analyzed by the computer 18 to determine whether ingesta or fecal contamination is present on the imaged carcass. This can be done, for example, by establishing a threshold value $\text{IF}_{thresh}$ which is indicative of contamination. In this case, calculated values $\text{IF}_i$ contained in the final output image data are compared with $\text{IF}_{thresh}$, and a decision is made based on such comparison. For example, a positive (contamination) judgment (Step 407) could be made if a single pixel value $\text{IF}_i$ exceeds the threshold value $\text{IF}_{thresh}$, as indicated in FIG. 4. Or a judgment of contamination could be made if a minimum number of values $\text{IF}_i$ exceed the threshold; or a minimum number within a defined proximity. Otherwise, the carcass is concluded to be contamination free (step 408).

Figure 5:
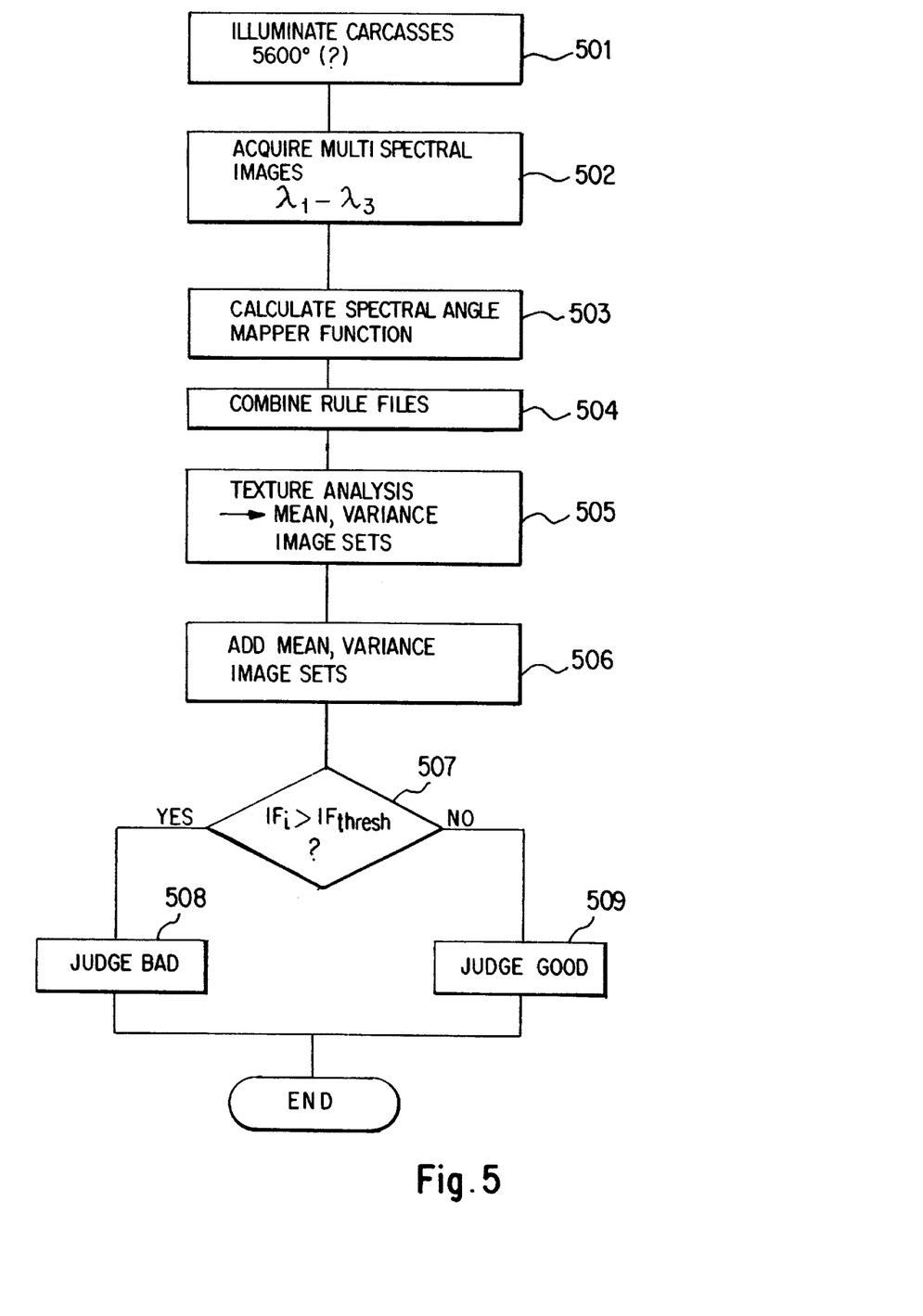
FIG. 5 is a flow chart which illustrates contaminant detection processing according to a second embodiment of the invention.

As noted previously, the technique for efficient detection of contaminants according to the invention differs if the carcasses have been soft scalded. As shown in FIG. 5, the carcasses are illuminated in step 501 by a 5600K color corrected light source in the same manner as indicated in FIG. 4. In this embodiment, however, three multispectral image data sets are acquired in step 502 by the cameras 12, as follows:

$\lambda_1 = 497-537$ nm
$\lambda_2 = 545-585$ nm
$\lambda_3 = 608-648$ nm

That is, DN reflectance values are determined for each pixel in each of the three wavelengths $\lambda_1 - \lambda_3$. Thus, each pixel is characterized by a spectral pattern or "signature" consisting of these three DN values—one for each wavelength.

Next, in step 503, an arithmetic function referred to as Spectral Angle Mapper is run, correlating each of the acquired data sets $\lambda$ with predetermined spectral signature values in the detected wavelengths $\lambda_1$, $\lambda_2$ and $\lambda_3$, for each of four types of ingesta/fecal (digestive) contamination, which differ only in their source within the digestic tract of the carcass prior to dressing; that is in particular, the stomach, the duodenum, the colon and the ceca. The reflectance values for each of these types of contaminants in the sample wavelengths varies in a characteristic fashion, and accordingly this characteristic pattern can be used to detect its presence. (It is of course apparent that the greater the number of wavelength bands which is used to characterize both the target carcass and the types of fecal contamination, the greater the precision of the correlation. However, it has been determined that the three wavelength values indicated above are sufficient in practice.)

The Spectral Angle Mapper (SAM) is a mathematical function which can be used to determine the degree of spectral similarity between the spectral signatures for each pixel in the acquired image data set and the corresponding spectral values for the four contaminants noted above. The formula for calculation of SAM is as follows:

$$\alpha = \cos^{-1}\left(\frac{\sum_{i=1}^{nb} t_i r_i}{\left(\sum_{i=1}^{nb} t_i^2\right)^{1/2} \left(\sum_{i=1}^{nb} r_i^2\right)^{1/2}}\right) \quad \text{(Eq. 4)}$$

wherein $t_i$ = detected reflectance value of the target carcass in the $i_{th}$ band;

$r_i$ = reflectance value of the subject contaminant in the $i_{th}$ band; and nb = number of bands i in the image.

In this case, since four different types of contaminants are to be detected, four values of $\alpha$ are calculated for each pixel—one for each of the respective reference spectra—resulting in four image data sets, referred to as Rule Files. By virtue of the SAM algorithm, the data in each of these Rule Files are indicative of the likelihood of contamination of the imaged carcass.

Next, in step 504 the sum or product of all the Rule Files produces a new image file. Thereafter, processing for soft scalded carcasses in FIG. 5 proceeds in the same manner as for soft scalded carcasses in FIG. 4. That is, a texture analysis is performed in step 505; the mean and variance values are combined in step 506 and a contamination determination based on the combined image data set in steps 507–509.

The optical inspection system according to the invention has a number of significant advantages in comparison to previously used visual inspection methods. In particular, it is more reliable in that it permits a faster and more complete inspection within extremely limited time period available while the birds are being processed on the conveyor line. In addition, the evaluation criteria are objective, eliminating the need for a subjective human judgment. Finally, use of the inspection system according to the invention may result in the reduction of water usage within the typical poultry processing plant by reducing the number of required washings per bird.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. Apparatus for detecting ingesta or fecal contamination on food items which are processed on a conveyor system, comprising:

a light sealed enclosure which excludes exterior ambient light from an interior thereof, said interior of said enclosure being adapted to surround at least a portion of said conveyor system;

at least one light source disposed in said enclosure, for illuminating each successive food item on said conveyor system with light having a predetermined spectral content; and at least one sensor which senses light reflected from said food items in a plurality of frequency bands, and which outputs signals indicative of reflected light intensity in each of said frequency bands wherein, said enclosure has an entrance and an exit by which said conveyor passes through said interior; and each of said entrance and said exit has a fixed structural configuration that defines a transport oath for said conveyor into and out of said interior, which fixed structural configuration excludes exterior ambient light from said interior.

2. Apparatus for detecting ingesta or fecal contamination on food items which are processed on a conveyor system, comprising:

a light sealed enclosure which excludes exterior ambient light from an interior thereof, said interior of said enclosure being adapted to surround at least a portion of said conveyor system;

at least one light source disposed in said enclosure, for illuminating each successive food item on said conveyor system with light having a predetermined spectral content;

at least one sensor which senses light reflected from said food items in a plurality of frequency bands, and which outputs signals indicative of reflected light intensity in each of said frequency bands; wherein said enclosure comprises, walls defining the interior of said light excluding enclosure; and an entrance and an exit for permitting said conveyor to pass through said interior; and wherein each of said entrance and said exit has a plurality of interdigitated light blocking baffles, defining a transport path for said conveyor, whereby exterior ambient light is excluded from said interior.

3. Apparatus for detecting contamination on food items according to claim 2, wherein:

said at least one light source comprises a plurality of light sources arranged sequentially along said conveyor, for illuminating food items on sequential segments of said conveyor; and said at least one sensor comprises a plurality of sensors, each being paired with a respective one of said light sources for detecting light therefrom that is reflected by a food item; and said apparatus further comprises a plurality of additional baffles arranged on said walls between adjacent pairs of light sources and sensors for preventing each of said sensors from detecting light scattered from a food item illuminated in a field of view of an adjacent sensor.

4. Apparatus for detecting contamination on food items according to claim 3, wherein said additional baffles are disposed substantially transversely to a direction of travel of food items on said conveyor.

5. Apparatus for detecting contamination on food items according to claim 3, wherein:

said plurality of light sources comprises light sources arranged on opposite sides of said conveyor;

said enclosure further comprises a longitudinal baffle disposed between sensors and cameras on opposite sides of said enclosure, whereby light from light sources on one side of said conveyor is prevented from propagating to and being detected by sensors situated on an opposite side of said conveyor; and shackles of said conveyor are swung alternately to opposite sides of said longitudinal baffle forming separate lines of food items on both sides of said longitudinal baffle.

6. Conveyor apparatus for processing food items, comprising:

a conveyor for transporting said food items for processing;

a light sealed enclosure which excludes exterior ambient light from an interior thereof, said interior of said enclosure surrounding at least a portion of said conveyor;

at least one light source disposed in said enclosure, for illuminating each successive food item on said conveyor with light having a predetermined spectral content; and at least one sensor disposed in said enclosure, for sensing light reflected from said food items and outputting signals indicative of reflected light intensity; wherein said enclosure has an entrance and an exit by which said conveyor passes through said interior; and each of said entrance and said exit has a fixed structural configuration that defines a transport path for said conveyor into and out of said interior, which fixed structural configuration excludes exterior ambient light from said interior.

7. Apparatus for detecting contamination on food items according to claim 6, wherein:

said at least one light source comprises a plurality of light sources arranged sequentially along said conveyor, for illuminating food items on sequential segments of said conveyor;

said at least one sensor comprises a plurality of sensors, each being paired with a respective one of said light sources for detecting light therefrom that is reflected by a food item; and said apparatus further comprises a plurality of additional baffles arranged on said walls between adjacent pairs of light sources and sensors for preventing each of said sensors from detecting light scattered from a food item illuminated in a field of view of an adjacent sensor.

8. Apparatus for detecting contamination on food items according to claim 7, wherein said additional baffles are disposed substantially transversely to a direction of travel of food items on said conveyor.

9. Conveyor apparatus for processing food items, comprising:

a conveyor for transporting said food items for processing;

a light sealed enclosure which excludes exterior ambient light from an interior thereof, said interior of said enclosure surrounding at least a portion of said conveyor;

at least one light source disposed in said enclosure, for illuminating each successive food item on said conveyor with light having a predetermined spectral content; and at least one sensor disposed in said enclosure, for sensing light reflected from said food items and outputting signals indicative of reflected light intensity; wherein said at least one light source comprises a plurality of light sources arranged sequentially along said conveyor, for illuminating food items on sequential segments of said conveyor;

said at least one sensor comprises a plurality of sensors, each being paired with a respective one of said light sources for detecting light therefrom that is reflected by a food item;

said apparatus further comprises a plurality of additional baffles arranged on said walls between adjacent pairs of light sources and sensors for preventing each of said sensors from detecting light scattered from a food item illuminated in a field of view of an adjacent sensor;

said plurality of light sources comprises light sources arranged on opposite sides of said conveyor;

said enclosure further comprises a longitudinal baffle disposed between sensors and cameras on opposite sides of said enclosure, whereby light from light sources on one side of said conveyor is prevented from propagating to and being detected by sensors situated on an opposite side of said conveyor; and shackles of said conveyor are swung alternately to opposite sides of said longitudinal baffle forming separate lines of food items on both sides of said longitudinal baffle.

10. In a system for detecting contamination on a food item which is supported and transported on a conveyor under control of a computer, during processing of said food item for consumption, the combination comprising:

a light sealed enclosure which excludes exterior ambient light from an interior thereof, said enclosure having a light excluding entrance and a light excluding exit adapted to accommodate transporting of said food item on said conveyor through said interior, each of said entrance and said exit having a fixed structural configuration that defines a transport oath for said conveyor into and out of said interior which fixed structural configuration excludes exterior ambient light from said interior;

at least one light source disposed in said interior of said enclosure, for illuminating said food item as it passes through said enclosure, with radiation having a predetermined spectral content;

at least one imaging device for acquiring image data indicative of radiation reflected from said food item within said enclosure; and a computer readable medium encoded with a program for causing said computer to control operation of said light source and said imaging device and movement of said food item through said light sealed enclosure by said conveyor, to acquire image information of said food item as it passes through said light sealed enclosure, and for processing said image information to generate an output which is indicative of contamination on said food item.

11. Apparatus for detecting contamination on food items according to claim 10, wherein:

said at least one light source comprises a plurality of light sources arranged sequentially along said conveyor, for illuminating food items on sequential segments of said conveyor; and said at least one imaging device comprises a plurality of sensors, each being paired with a respective one of said light sources for detecting light therefrom that is reflected by a food item; and said apparatus further comprises a plurality of additional baffles arranged on said walls between adjacent pairs of light sources and imaging devices for preventing each of said imaging devices from detecting light scattered from a food item illuminated in a field of view of an adjacent imaging device.

12. Apparatus for detecting contamination on food items according to claim 11, wherein said additional baffles are disposed substantially transversely to a direction of travel of food items on said conveyor.

13. In a system for detecting contamination on a food item which is supported and transported on a conveyor under control of a computer, during processing of said food item for consumption, the combination comprising:

a light sealed enclosure which excludes exterior ambient light from an interior thereof, said enclosure having a light excluding entrance and a light excluding exit adapted to accommodate transporting of said food item on said conveyor through said interior, each of said entrance and said exit having a fixed structural configuration that defines a transport oath for said conveyor into and out of said interior, which fixed structural configuration excludes exterior ambient light from said interior;

at least one light source disposed in said interior of said enclosure, for illuminating said food item as it passes through said enclosure, with radiation having a predetermined spectral content;

at least one imaging device for acquiring image data indicative of radiation reflected from said food item within said enclosure; and a computer readable medium encoded with a program for causing said computer to control operation of said light source and said imaging device and movement of said food item through said light sealed enclosure by said conveyor, to acquire image information of said food item as it passes through said light sealed enclosure, and for processing said image information to generate an output which is indicative of contamination on said food item, wherein:

said at least one light source comprises a plurality of light sources arranged sequentially along said conveyor, for illuminating food items on sequential segments of said conveyor; and said at least one imaging device comprises a plurality of sensors, each being paired with a respective one of said light sources for detecting light therefrom that is reflected by a food item;

said apparatus further comprises a plurality of additional baffles arranged on said walls between adjacent pairs of light sources and imaging devices for preventing each of said imaging devices from detecting light scattered from a food item illuminated in a field of view of an adjacent imaging device;

said additional baffles are disposed substantially transversely to a direction of travel of food items on said conveyor;

said plurality of light sources comprises light sources arranged on opposite sides of said conveyor;

said enclosure further comprises a longitudinal baffle disposed between sensors and cameras on opposite sides of said enclosure, whereby light from light sources on one side of said conveyor is prevented from propagating to and being detected by sensors situated on an opposite side of said conveyor; and shackles of said conveyor are swung alternately to opposite sides of said longitudinal baffle forming separate lines of food items on both sides of said longitudinal baffle.

14. The system according to claim 10, wherein said output is a processed image which shows a visual indication of contamination.

15. The system according to claim 10, wherein said computer automatically detects presence of contamination based on said output.

16. The system according to claim 10, wherein said contamination is digestive contamination.

17. In a system for detecting contamination on a food item which is supported and transported on a conveyor under control of a computer, during processing thereof for consumption, the combination comprising:

a light sealed enclosure which excludes exterior ambient light from an interior thereof, said enclosure having a light excluding entrance and a light excluding exit adapted to accommodate transporting of said food item through said interior, each of said entrance and said exit having a fixed structural configuration that defines a transport oath for said conveyor into and out of said interior, which fixed structural configuration excludes exterior ambient light from said interior;

a conveyor for supporting and transporting said food item through said light sealed inclosure while it is being processed for consumption;

at least one light source for illuminating said food item in said interior of said enclosure, with radiation having a predetermined spectral content;

at least one imaging device for acquiring image data indicative of radiation reflected from said food item within said enclosure; and a computer readable medium encoded with a program for causing said computer to control operation of said conveyor, said light source and said imaging device to acquire image information of said food item as it passes through said light sealed enclosure, for generating an output which is indicative of contamination on said food item.

18. Apparatus for detecting contamination of food item according to claim 17, wherein:

said at least one light source comprises a plurality of light sources arranged sequentially along said conveyor, for illuminating food items on sequential segments of said conveyor; and said at least one sensor comprises a plurality of sensors, each being paired with a respective one of said light sources for detecting light therefrom that is reflected by a food item; and said apparatus further comprises a plurality of additional baffles arranged on said walls between adjacent pairs of light sources and sensors for preventing each of said sensors from detecting light scattered from a food item illuminated in a field of view of an adjacent sensor.

19. Apparatus for detecting contamination on food items according to claim 18, wherein said additional baffles are disposed substantially transversely to a direction of travel of food items on said conveyor.

20. In a system for detecting contamination on a food item during processing thereof for consumption, the combination comprising:

a light sealed enclosure which excludes exterior ambient light from an interior thereof, said enclosure having a light excluding entrance and a light excluding exit adapted to accommodate transporting of said food item through said interior;

a conveyor for supporting and transporting said food item through said light sealed enclosure while it is being processed for consumption;

at least one light source for illuminating said food item in said interior of said enclosure, with radiation having a predetermined spectral at least one imaging device for acquiring image data indicative of radiation reflected from said food item within said enclosure; and a computer readable medium encoded with a program for causing said computer to control operation of said conveyor, said light source and said imaging device to acquire image information of said food item as it passes through said light sealed enclosure, for generating an output which is indicative of contamination on said food item; wherein, said at least one light source comprises a plurality of light sources arranged sequentially along said conveyor, for illuminating food items on sequential segments of said conveyor;

said at least one sensor comprises a plurality of sensors, each being paired with a respective one of said light sources for detecting light therefrom that is reflected by a food item; and said apparatus further comprises a plurality of additional baffles arranged on said walls between adjacent pairs of light sources and sensors for preventing each of said sensors from detecting light scattered from a food item illuminated in a field of view of an adjacent sensor;

said plurality of light sources comprises light sources arranged on opposite sides of said conveyor;

said enclosure further comprises a longitudinal baffle disposed between sensors and cameras on opposite sides of said enclosure, whereby light from light sources on one side of said conveyor is prevented from propagating to and being detected by sensors situated on an opposite side of said conveyor; and shackles of said conveyor are swung alternately to opposite sides of said longitudinal baffle forming separate lines of food items on both sides of said longitudinal baffle.

21. The system according to claim 20, wherein said output is a processed image which shows a visual indication of contamination.

22. The system according to claim 20, wherein said computer automatically detects presence of contamination based on said output.

23. The system according to claim 20, wherein said contamination is digestive contamination.

* * * * *